US008642089B2

(12) United States Patent
Petereit et al.

(10) Patent No.: US 8,642,089 B2
(45) Date of Patent: Feb. 4, 2014

(54) MELT EXTRUSION OF SALTS OF ACTIVE INGREDIENTS

(75) Inventors: Hans-Ulrich Petereit, Darmstadt (DE); Christian Meier, Darmstadt (DE); Andreas Gryczke, Buettelborn (DE)

(73) Assignee: Evonik Roehm GmbH, Darmstadt (DE)

( * ) Notice: Subject to any disclaimer, the term of this patent is extended or adjusted under 35 U.S.C. 154(b) by 2367 days.

(21) Appl. No.: 10/498,829

(22) PCT Filed: Jan. 30, 2003

(86) PCT No.: PCT/EP03/00935
§ 371 (c)(1),
(2), (4) Date: Jun. 24, 2004

(87) PCT Pub. No.: WO03/072083
PCT Pub. Date: Sep. 4, 2003

(65) Prior Publication Data
US 2004/0253314 A1    Dec. 16, 2004

(30) Foreign Application Priority Data
Feb. 27, 2002 (DE) .................................. 102 08 344

(51) Int. Cl.
*A61K 9/16* (2006.01)
*A61K 9/00* (2006.01)
*A61K 9/14* (2006.01)
*A61K 9/50* (2006.01)
*A61K 47/32* (2006.01)

(52) U.S. Cl.
USPC ........... 424/489; 424/400; 424/487; 424/501; 514/772.6

(58) Field of Classification Search
USPC ............... 424/400, 487, 489, 501; 514/772.6
See application file for complete search history.

(56) References Cited

U.S. PATENT DOCUMENTS

| | | | | |
|---|---|---|---|---|
| 4,795,643 A | * | 1/1989 | Seth | .............................. 424/456 |
| 5,084,278 A | * | 1/1992 | Mehta | ............................ 424/441 |
| 5,695,781 A | * | 12/1997 | Zhang et al. | .................... 424/468 |
| 5,958,452 A | * | 9/1999 | Oshlack et al. | ................ 424/457 |
| 5,965,161 A | * | 10/1999 | Oshlack et al. | ................ 424/457 |
| 6,576,255 B1 | | 6/2003 | Petereit et al. | |
| 6,743,442 B2 | * | 6/2004 | Oshlack et al. | ................ 424/456 |
| 2001/0031278 A1 | | 10/2001 | Oshlack et al. | |
| 2001/0036476 A1 | | 11/2001 | Oshlack et al. | |
| 2003/0064036 A1 | | 4/2003 | Petereit et al. | |
| 2004/0249035 A1 | | 12/2004 | Petereit et al. | |

FOREIGN PATENT DOCUMENTS

| | | | | |
|---|---|---|---|---|
| WO | WO 93/07859 | * | 4/1993 | ............... A61K 9/16 |
| WO | 00/35450 | | 6/2000 | |

OTHER PUBLICATIONS

Jorg Breitenbach, "Melt extrusion: from process to drug delivery technology", European Journal of Pharmaceutics and Biopharmaceutics, Sep. 2002, 54, 107-117.*

K. A. Mehta, M. S. Kislalioglu, W. Phuapradit, A. W. Malick, and N. H. Shah, "Release performance of a poorly soluble drug from a novel, Eudragit-based multi-unit erosion matrix", International Journal of Pharmaceutics, 2001, 213, 7-12.*

David N. John, Stephen Fort, Malcolm J. Lewis & David K. Luscombe, "Pharmacokinetics and pharmacodynamics of verapamil following sublingual and oral administration to healthy volunteers", British Journal of Clinical Pharmacology, 1992, 33, 623-627.*

* cited by examiner

*Primary Examiner* — Abigail Fisher
*Assistant Examiner* — Nathan W Schlientz
(74) *Attorney, Agent, or Firm* — Oblon, Spivak, McClelland, Maier & Neustadt, L.L.P.

(57) ABSTRACT

The invention relates to a method for producing active ingredient-containing granules or powders involving the following steps: a) melting a mixture consisting of a pharmaceutical active ingredient and of a (meth)acrylate copolymer, which is comprised of 40 to 75 wt. % of radically polymerized C1 to C4 alkyl esters of acrylic acid or of methacrylic acid and can be comprised of 25 to 60 wt. % (meth)acrylate monomers having an anionic group in the alkyl radial; b) extruding the mixture, and; c) comminuting the extrudate to form a granule or powder. The inventive method is characterized in that the active ingredient is the salt of an alkaline substance, and in that the pH value, which can be measured on the obtained powder or granule, is equal to or less than pH 7.0. The invention also relates to pharmaceutical dosage forms or precursors thereof, which can be produced using the inventive method.

26 Claims, No Drawings

MELT EXTRUSION OF SALTS OF ACTIVE INGREDIENTS

FIELD OF THE INVENTION

The invention relates to a process for the production of taste-isolated, active ingredient-containing granules or powders by melting a mixture of a (meth)acrylate copolymer having anionic groups and of a pharmaceutical active ingredient, extrusion of the mixture comminution of the extrudate to give granules or powder.

PRIOR ART

EP-A 0 417 588 describes a process for the production of a complexed medicament from an ionic active ingredient by reaction of the active ingredient with a complementary ionic, particulate polymer in the presence of an amount of water sufficient for the moistening of the mixture. With salts of active ingredients, it is necessary to add an acid or base to the mixture for the neutralization of the counterion of the active ingredient. In the case of the reaction of salts of active ingredients such as propranolol HCl, verapamil HCl or metoclopramide HCl with anionic (meth)acrylate copolymers such as EUDRAGIT® L or EUDRAGIT® L100-55, sodium carbonate, for example, is added to the mixture. By means of the reaction of the active ingredient with the complementary ionic polymer, it is generally possible to achieve a taste isolation of bitter-tasting active ingredients.

WO 01/43935 describes a process for the production of molded bodies by means of injection molding by melting a mixture of a (meth)acrylate copolymer which is composed of 40 to 100% by weight of free radical-polymerized $C_1$- to $C_4$-alkyl esters of acrylic or of methacrylic acid and 0 to 60% by weight of (meth)acrylate monomers having an anionic group in the alkyl radical, which contains 0.1 to 3% by weight of a release agent, where, if appropriate, 0 to 50% by weight of a dry extender, 0 to 30% by weight of a plasticizer, 0 to 100% by weight of additives or excipients, 0 to 100% by weight of a pharmaceutical active ingredient, 0 to 20% by weight of a further polymer or copolymer can be present in the mixture, the mixture having a content of low-boiling constituents having a vapor pressure of at least 1.9 bar at 120° C. of above 0.5% by weight before melting.

In a further process step, degassing of the mixture takes place in the thermoplastic state at temperatures of at least 120° C., whereby the content of the low-boiling constituents having a vapor pressure of at least 1.9 bar at 120° C. is lowered to at most 0.5% by weight. Subsequently, spraying of the fused and degassed mixture into the molding cavity of an injection molding tool takes place, the molding cavity having a temperature which is at least 10° C. below the glass transition temperature of the (meth)acrylate copolymer, cooling of the melt mixture and removal of the resulting molded body from the mold. The process is generally suitable for the processing of a large number of active ingredients, such as, for example, verapamil, and their pharmaceutically used salts.

EP 0 704 207 A2 describes thermoplastic plastics for intestinal juice-soluble pharmaceutical coatings. These are copolymers of 16 to 40% by weight of acrylic or methacrylic acid, 30 to 80% by weight of methyl acrylate and 0 to 40% by weight of other alkyl esters of acrylic acid and/or methacrylic acid.

The minimum film formation temperature (MFT according to DIN 53 778) is in the range between 0 and 25° C., such that processing at room temperature without addition of plasticizer is possible. The tensile extension of the films, measured according to DIN 53 455, is as a rule 50% or more at a content of at most 10% by weight of triethyl citrate. The copolymers can be processed by means of melt extrusion, e.g. to give films, into which pharmaceutical cores are incorporated later. The possibility of the immediate incorporation of active ingredients during extrusion is not considered.

Object And Achievement

In the production of pharmaceutical forms, as a rule it is attempted to keep low the number of substances employed and also to keep low or, as far as possible, to avoid completely quantitative additions of excipients such as, for example, plasticizers or release agents. By this means, any possible incompatibility problems, undesired interactions or other imponderables can be kept low or excluded from the start. For this approach, the process described in EP-A 0 417 588 offers a good starting point, since the pharmaceutical forms as a rule only contain the active ingredient and a complementary ionic polymer.

According to EP-A 0 417 588, an isolation of the taste of bitter-tasting active ingredients can be achieved by reaction of an active ingredient with a complementary ionic, particulate polymer in the presence of an amount of water sufficient for the moistening of the mixture. The granular masses obtained are subsequently converted into active ingredient-containing powders or pastes by drying. The addition of further pharmaceutical excipients is as a rule not necessary here with the exception that in the case of salts of active ingredients an acid or base is to be added to the mixture for the neutralization of the counterion of the active ingredient.

As an undesired side effect, in the case of basic active ingredient salts having an acidic counterion such as, for example, verapamil HCl, a slightly alkaline pH is established by means of the neutralization with a base, which produces an undesired soap-like taste. Moreover, the alkaline pH can lead to undesired interactions with the active ingredient occurring over time and the long-term storage stability of the pharmaceutical forms obtained being adversely affected.

Starting from this problem, it was regarded as an object to make available a taste isolation for basic salts of active ingredients, in which an addition of excipients generally and in particular of substances having a basic action can be avoided. Production should be simplified compared with EP-A 0 417 588. The resulting formulations of the taste-isolated active ingredients should moreover have a comparatively improved long-term storage stability.

The process according to WO 01/43935 is in this case not suitable, since during the injection molding processing the addition of release agents is absolutely necessary. During the processing of (meth)acrylate copolymers having relatively high contents of anionic radicals, such as are regarded as necessary for complexing of active ingredients, the addition of plasticizers is moreover unavoidable.

The object is achieved by a
process for the production of active ingredient-containing granules or powders by means of the steps
  a) melting of a mixture of a pharmaceutical active ingredient and of a (meth)acrylate copolymer which consists of 40 to 75% by weight of free radical-polymerized Cl- to $C_4$-alkyl esters of acrylic or of methacrylic acid and can 25 to 60% by weight of (meth)acrylate monomers having an anionic group in the alkyl radical,
  b) extrusion of the mixture
  c) comminution of the extrudate to give granules or powder characterized in that the active ingredient is the salt of a basic substance and in that the pH measurable on the powder or granules obtained is pH 7.0 or less than pH 7.0.

It has now been found that the salt of a basic substance can be processed to give taste-isolated granules or powders in the course of melt preparation by extrusion as a mixture with a (meth)acrylate copolymer having anionic radicals without the addition of substances having a basic action. By this means, the pH of the powder or granules obtained can be pH 7.0 or less than pH 7.0, such that an environment more favorable for the long-term storage stability of the active ingredient is obtained.

High amounts of further additives, e.g. plasticizers or release agents, such as would be necessary for injection molding processing, can be avoided.

CARRYING OUT THE INVENTION

The invention relates to a process for the production of active ingredient-containing granules or powders by means of the steps
  a) melting of a mixture of a pharmaceutical active ingredient and of a (meth)acrylate copolymer which consists of 40 to 75% by weight of free radical-polymerized $C_1$- to $C_4$-alkyl esters of acrylic or of methacrylic acid and can 25 to 60% by weight of (meth)acrylate monomers having an anionic group in the alkyl radical,
  b) extrusion of the mixture
  c) comminution of the extrudate to give granules or powder characterized in that
the active ingredient is the salt of a basic substance and in that the pH measurable on the powder or granules obtained is pH 7.0 or less than pH 7.0.

(Meth)acrylate Copolymers Having Anionic Radicals

The (meth)acrylate copolymer consists to 40 to 80, preferably to 45 to 75, in particular to 55 to 65, % by weight of free radical-polymerized $C_1$- to $C_4$-alkyl esters of acrylic or of methacrylic acid and to 20 to 60, preferably 25 to 58, in particular 45 to 55, % by weight of (meth)acrylate monomers having an anionic group present in the alkyl radical.

As a rule, the proportions add up to 100% by weight. It is understood, however, that additionally, without this leading to an adverse effect on or change in the essential properties, small amounts in the range from 0 to 10, e.g. 1 to 5, % by weight of further vinylically copolymerizable monomers can be present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group in the alkyl radical can be, for example, acrylic acid, but preferably methacrylic acid.

EUDRAGIT® L or EUDRAGIT® L100-55 Types

Anionic (meth)acrylate copolymers of 40 to 60% by weight of methacrylic acid and 60 to 40% by weight of methyl methacrylate or 60 to 40% by weight of ethyl acrylate (EUDRAGIT® L (50% by weight of methyl methacrylate and 50% by weight of methacrylic acid) or EUDRAGIT® L100-55 (50% by weight of ethyl acrylate and 50% by weight of methacrylic acid) types) are suitable.

EUDRAGIT® S Type

Anionic (meth)acrylate copolymers of 20 to 40% by weight of methacrylic acid and 80 to 60% by weight of methyl methacrylate (EUDRAGIT® S type) are suitable.

EUDRAGIT® Type Having a Medium Content of Methacrylic Acid.

Anionic (meth)acrylate copolymers of 20 to 34% by weight of methacrylic acid and/or acrylic acid, 20 to 69% by weight of methyl acrylate and 0 to 40% by weight of ethyl acrylate and optionally 0 to 10% by weight of further vinylically copolymerizable monomers, with the proviso that the glass transition temperature of the copolymer according to ISO 11357-2, item 3.3.3, is at most 60° C., are likewise suitable.

The copolymer is composed in particular of free radical-polymerized units of
20 to 34, preferably 25 to 33, particularly preferably 28 to 32, % by weight of methacrylic acid or acrylic acid; methacrylic acid is preferred,
20 to 69, preferably 35 to 65, particularly preferably 35 to 55, % by weight of methyl acrylate and optionally 0 to 40, preferably 5 to 35, particularly preferably 15 to 35, % by weight of ethyl acrylate, with the proviso that the glass transition temperature of the copolymer (without addition of plasticizer) according to ISO 11357-2, item 3.3.3, is at most 60, preferably 40 to 60, particularly preferably 45 to 55° C.

The copolymer preferably consists essentially to exclusively of the monomers methacrylic acid, methyl acrylate and ethyl acrylate in the quantitative proportions indicated above. As a rule, the proportions mentioned add up to 100% by weight. It is additionally possible, however, without this leading to an adverse effect on or change in the essential properties, for small amounts in the range from 0 to 10, e.g. 1 to 5, % by weight of further vinylically copolymerizable monomers, such as, for example, methyl methacrylate, butyl methacrylate, butyl acrylate or hydroxyethyl methacrylate to be present.

Preparation of the (Meth)acrylate Copolymers

The (meth)acrylate copolymers are obtained in a manner known per se by free radical substance, solution, bead or emulsion polymerization. They must be brought into the desired particle size range before processing by means of suitable grinding, drying or spraying processes. This can be carried out by simple breaking of extruded and cooled strands of granules or die-face pelletization.

In particular when mixing with further powders or liquids, the use of powders can be advantageous. Suitable implements for the production of the powders are familiar to the person skilled in the art, e.g. air jet mills, pinned disk mills, fan mills. Optionally, appropriate sieving steps can be included. A suitable mill for large industrial amounts is, for example, an opposed jet mill (Multi No. 4200), which is operated at about 6 bar overpressure.

Basic Salts of Active Ingredients

The basic salts of active ingredients can be, for example, verapamil HCl. Preferably, the pH of the resulting verapamil-containing granules or powder is pH 2.3 to pH 4.5.

Processing by Means of Melt Extrusion

The production of active ingredient-containing granules or powders is carried out by means of the steps
  a) melting of a mixture of a pharmaceutical active ingredient and of a (meth)acrylate copolymer which consists of 40 to 75% by weight of free radical-polymerized $C_1$- to $C_4$-alkyl esters of acrylic or of methacrylic acid and can 25 to 60% by weight of (meth)acrylate monomers having an anionic group in the alkyl radical,
  b) extrusion of the mixture, preferably in an extruder, e.g. a double-screw extruder having synchronous or opposing screws.
  c) comminution of the extrudate to give granules or powder, e.g. by die-face pelletization of the extrudate or grinding of the granules.

Quantitative Ratios

The quantitative ratio of active ingredient to (meth)acrylate copolymer can be, for example, 10 to 1 to 1 to 10, preferably 10 to 2 to 2 to 10, particularly preferably 10 to 3 to 3 to 10, based on parts by weight.

Excipients

The process according to the invention makes it possible to decrease the number and quantitative proportions of otherwise customary pharmaceutical excipients or even to dispense with these. If additives are to be used at all, these can be added to the mixture (process step a)) before or after melting or alternatively during extrusion (process step b)) in the extruder.

Release Agents (Mold Release Agents)

Preferably, no or less than 0.1% by weight of release agent is added to the mixture are.

Examples of release agents (mold release agents) are: esters of fatty acids or fatty acid amides, aliphatic, long-chain carboxylic acids, fatty alcohols and their esters., montan or paraffin waxes and metal soaps; particular mention should be made of e.g. glycerol monostearate, stearyl alcohol, glycerol behenic acid ester, cetyl alcohol, palmitic acid, carnauba wax, beeswax.

Plasticizers:

Preferably, no or less than 0.5% by weight of plasticizers is added to the mixture are.

Substances suitable as plasticizers as a rule have a molecular weight of between 100 and 20,000 and contain one or more hydrophilic groups in the molecule, e.g. hydroxyl, ester or amino groups. Citrates, phthalates, sebacates, castor oil are suitable. Examples of plasticizers are alkyl citrates, propylene glycol, glycerol esters, alkyl phthalates, alkyl sebacates, sucrose esters, sorbitan esters, diethyl sebacate, dibutyl sebacate and polyethylene glycols 4000 to 20,000. Preferred plasticizers are tributyl citrate, triethyl citrate, acetyltriethyl citrate, dibutyl sebacate and diethyl sebacate.

Dry Extenders (Antiadhesive Agents)

Preferably, no or less than 0.1% by weight of dry extenders (antiadhesive agents) is added are.

Dry extenders have the following properties: they have large specific surface areas, are chemically inert, and are readily pourable and finely divided. On account of these properties, they can advantageously be dispersed homogeneously in melts and reduce the tackiness of polymers which are prone to tackiness, e.g. on account of relatively high contents of anionic radicals.

Examples of dry extenders are: alumina, magnesium oxide, kaolin, talc, silicic acid (Aerosils), barium sulfate, carbon black and cellulose.

Further Pharmaceutically Customary Excipients

Preferably, no or less than 10% by weight, preferably less than 2% by weight, of the further pharmaceutically customary excipients mentioned below, such as stabilizers, colorants, antioxidants, wetting agents, pigments and lustering agents, are added to the mixture.

Processing Temperatures

The processing temperature in process steps a) and b) can be in the range from 50 to 200° C., preferably in the range from 80 to 180° C. Depending on the copolymer employed, the processing temperature can be 0 to 100, particularly preferably 10 to 50, ° C. above its glass transition temperature $T_{mg}$ (without plasticizer addition, according to ISO 11357-2, item 3.3.3). In the case of very strongly plasticizing active ingredients, e.g. chlorpheniramine maleate, a processing temperature up to 50° C. below the glass transition temperature can also be appropriate.

Granules and Powders

Active ingredient-containing granules or powders can be produced by the process according to the invention which contain the basic active ingredient in complexed form. The precise molecular mechanism of complexation and the exact structure of the complexes are not known.

In the dry product produced according to the invention, the active ingredient contained is present largely, as a rule to more than 90%, preferably to more than 95%, in particular to more than 97%, in the form of a complex with the polymer. The proportion of the active ingredient which is not complex-bound can be determined if the product is taken up in water, the solution is filtered and the active ingredient content in the filtrate is determined. The uncomplexed portion can, if necessary, be removed from the product in the same way.

The active ingredient-containing granules or powders contain no or less than 0.1% by weight of release agents.

The active ingredient-containing granules or powders contain no or less than 0.5% by weight of plasticizers. The active ingredient-containing granules or powders contain no or less than 0.1% by weight of dry extenders (antiadhesives).

The active ingredient-containing granules or powders contain no or less than 10% by weight of further pharmaceutically customary excipients, such as stabilizers, colorants, antioxidants, wetting agents, pigments and lustering agents.

Granules can be obtained, for example, by die-face pelletization of extrudate strands. The mean particle sizes of the granules are preferably in the range from 1 to 5 mm.

Powders can be obtained by grinding granules, e.g. in pinned disk mills. The mean particle sizes of the powders are preferably in the range from 1 to 1000 µm.

PHS

The pH which can be measured on the powders or granules obtained is pH 7.0 or if less than pH 7.0, the pH is preferably 2.5 to 6.0, particularly preferably 3 to 5.

If verapamil HCl is employed as the active ingredient salt, the pH of the granules or powder should preferably be pH 2.3 to pH 4.5, particularly preferably pH 2.5 to 3.5.

The pHs can be measured, for example, in a 1% strength suspension in purified water at room temperature using a pH measuring stick or a pH measuring electrode.

Bittering Powers

Bittering powers can be determined according to DAB (German pharmacopeia) 1999 method 2.8.N8 (determination of the bittering power). The bittering powers measured on the powders and granules are in the range between 1000 and 2000, preferably less than 1000.

The masking of the unpleasant, in particular bitter, taste of an active ingredient is one of the essential aims of the process. As a measure of the taste intensity, the bittering power according to DAB 1999 method 2.8.N8 (determination of the bittering power) can be used. The decrease in the bitter taste sensation is approximately proportional to the proportion bound; whereas, for example, pure verapamil HCl has a bittering power of over 100,000, the value for the complex having 90% of bound active ingredient is below 5000 and having 97% of bound active ingredient below 1000. A bittering power of 1000 is as a rule adequate for pharmaceutical practice. The degree of complexation necessary for this depends on the bittering power of the pure active ingredient and on its concentration in the administration form.

Active Ingredients

The active ingredients to be used according to the invention are salts of basic substances. The invention can advantageously be used for the following basic substances in salt form, preferably for those having a bitter taste, i.e. a bittering power of at least 100, preferably 1000, in particular 5000, measured on the pure active ingredient, from the classes of active ingredient indicated.

The active ingredients which can be employed according to the invention, which is salts of a basic substance, can belong, for example, to the active ingredient class of the analgesics, antirheumatics, psycho-pharmaceuticals, antibiotics, beta-blockers, anti-diabetics, H1 antihistaminics, H2 antihistaminics and/or vitamins.

Within these classes of active ingredient, the following active ingredients may be mentioned in particular:

Analgesics and Antirheumatics:

levacetylmethadol hydrochloride, oxycodone hydro-chloride, oxycodone hydrochloride 3-water, tramadol hydrochloride, tilidine hydrochloride Psychopharmaceuticals:

prometazine embonate; prometazine hydrochloride, prometazine teoclate, donepezil hydrochloride, nefazodone hydrochloride, reboxetine mesilate, sertraline hydrochloride Antibiotics:

Erythromycin acistrate, erythromycin estolate, erythromycin ethylsuccinate, erythromycin glucoheptonate, erythromycin lactobionate, erythromycin propionate, erythromycin stearate, erythromycin stinoprate, grepafloxacin hydrochloride, ciprofloxacin hydrochloride 1-water, levofloxacin hydrochloride, levofloxacin lactate, trovafloxacin mesylate, nevirapine hydrochloride, chlorhexidine acetate, chlorhexidine diacetate hydrate; chlorhexidine dihydrochloride, chlorhexidine digluconate, chlorhexidine gluconate, metronidazole benzoate, tetracycline hydrochloride, tetracycline phosphate, chlortetracycline hydro-chloride, oxytetracycline hydrochloride, doxycycline hyclate, minocycline hydrochloride hydrate, neomycin sulfate, tobramycin sulfate, clindamycin hydrochloride, moxifloxacin hydrochloride, indinavir sulfate, saquinavir mesylate, nelfinavir mesylate, amatidine hydrochloride, streptomycin sulfate, amikacin bis-hydrogensulfate, paromomycin sulfate, tobramycin sulfate Beta-Blockers propanolol hydrochloride, metoprolol tartrate, metoprolol fumarate, bisoprolol fumarate, nebivolol hydrochloride, betaxolol hydrochloride, tertatolol hydrochloride, bopindolol malonate, esmolol hydrochloride, oxprenolol hydrochloride Antidiabetics:

metformin hydrochloride, piogitazone hydrochloride, rosiglitazone maleate

H1 Antihistaminics:

diphenhydramine acefyllinate, diphenhydramine citrate, diphenhydramine hydrochloride, diphenhydramine mesilate, fexofenadine hydrochloride H2 Antihistaminics:

cimetidine hydrochloride, ticlopidine hydrochloride, ranitidine hydrochloride, roxatidine acetate Vitamins:

thiamine disulfide, thiamine disulfide O,O-dinicotinate, thiamine hydrobromide, thiamine hydrochloride, thiamine nitrate Others:

quinidine gluconate; hydrogensulfate-4-water; quinidine lactate, quinidine nitrite, quinidine polygalacturonate, quinidine sulfate, quinidine sulfate 2-water, amiloprilose, pseudoephedrine hydrochloride, sildenafil citrate, granisetrone hydrochloride, quinine sulfate 2-water; quinine monohydrochloride 2-water, metoclopramide dihydrochloride 1-water; metoclopramide hydrochloride, pentoxyverine dihydrogencitrate; pentoxyverine hydrochloride Examples of bitter-tasting active ingredients which show instabilities in basic to slightly alkaline medium (above pH 7):

erythromycin estolate, chlortetracycline hydrochloride, ranitidine hydrochloride, streptomycin sulfate, amikacin bis(hydrogensulfate), neomycin sulfate paromomycin sulfate, tobramycin sulfate Use The active ingredient-containing granules or powders which can be prepared by the process according to the invention can be used for the production of pharmaceutical forms, preferably for taste isolation.

Examples of pharmaceutical forms are: pellets, tablets or sachets with and without controlled release of active ingredient, liquid pharmaceutical forms, e.g. syrups, drops, suspensions. These pharmaceutical forms can further customary pharmaceutical excipients which, however, must be selected such that undesired ionic interactions with the powders or granules according to the invention are excluded, because they can increase the bittering power even in the pharmaceutical form, e.g. during storage.

EXAMPLES

For the preparation of the hot melt compound, an 18 mm, synchronous, double-screw extruder having an overall length of 40D is used (type: Micro 18 GL-40D Pharma, Leistritz Extrusionstechnik GmbH, Nuremberg). The supply of the powdered raw materials is carried out individually via continuously, gravimetrically operating metering devices. The nozzle diameter is 1.5 mm. The extruder is subdivided 9 separately temperature-controllable cylinders. The intake cylinder is fundamentally cooled such that the temperature remains below 10° C. In the 4th cylinder is situated a supply opening, which is utilized for the addition of liquids which may be necessary. Fundamentally, the arrangement of the cylinders is freely selectable. The strands obtained are cooled with air on a withdrawal belt and cut to give cylindrical granule grains having a diameter of about 1.5 mm and a length of 2-3 mm by means of a strand pelletizer (RCP-2.0 type, Randcastle Extrusions Systems Inc., Cedar Grove, N.Y., USA).

The granules are ground in an analytical mill (type A10, IKA-Labortechnik, Janke & Kunkel GmbH & Co. KG, Staufen, Germany) for a period of about 1 min.

Subsequently, the fine fraction under 315 µm is separated off and employed for further tests.

The bittering power is determined according to DAB 1999, 2.8.N8 (Determination of the bittering power) without inclusion of the personal correction factor.

Tensile strength of the tablets: fracture resistance tester (Pharmatest)

Disintegration of the tablets: DAB 2000

Active ingredient release according to USP 24 NF 19 at 50 rpm in HCl.

Example 1

Taste Isolation of a Cationic Active Ingredient Salt at a Molar Ratio of the Functional Groups in the Polymer to Verapamil of 1 mol to 0.38 mol A hot melt compound is produced from 50 parts by mass of verapamil HCl and 50 parts by mass of EUDRAGIT® L 100-55 (copolymer of 50% by weight of ethyl acrylate and 50% by weight of methacrylic acid). The temperature of the extruder cylinder was kept between 120° C. and 130° C. The speed of rotation of the screw was 300/min, the throughput was about 700 g/h. The mean residence time of the material in the extruder was about 4 min.

The granules produced from this extrusion process are slightly yellowish-colored and clear to slightly milky clouded. 10 granule grains leave behind only a slightly bitter taste in the mouth after 30 seconds. A bittering power of under 10 is determined for the ground powder.

This corresponds to a reduction of the bittering power for pure verapamil HCl by a power of 10.

If 800 mg of the ground powder are stirred into 50 ml of completely demineralized water (corresponding to 8 mg of verapamil per milliliter of water), a pH of 3 is determined.

Example 2

Production of Neutral-Taste Verapamil Tablets 160 g of the ground hot melt compound described in example 1, 230 g of lactose D20, 180 g of Avicel PH 102, 30 g of Explotab® were mixed for 15 min in a double cone mixer at a speed of rotation of about 30/min and added through a sieve having a 1 mm mesh width. After this, 3 g of magnesium stearate are added and the mixture is mixed for a further 5 min.

The powder mixture is compressed to give tablets on a 1-die eccentric press (EKO type, Korsch, Berlin) at a pressure of about 155 MPa (35 tablets/min). The nominal weight is adjusted to 603 mg (corresponding to 80 mg of verapamil HCl).

Properties of the tablets:
Diameter 11.1 mm
Tensile strength: about 2.37 N/mm$^2$
Weight 600 mg (s: 3 mg)

The tablets obtained leave behind no bitter taste in the mouth after saliva wetting for 10 s. The release of active ingredient was about 28% after 30 min and about 54% after 60 min.

Example 3

Taste Isolation of a Cationic Active Ingredient Salt at a Molar Ratio of the Functional Groups in the Polymer to Verapamil of 1 Mol to 0.3 Mol A hot melt compound is produced from 30 parts by mass of verapamil HCl and 70 parts by mass of a copolymer of 40% by weight of methyl acrylate, 30% by weight of ethyl acrylate and 30% by weight of methacrylic acid.

The temperature of the extruder cylinder was kept between 140° C. and 150° C. The speed of rotation of the screw was 136/min, the throughput was about 600 g/h. The mean residence time of the material in the extruder was about 4½ min. The granules produced from this extrusion process are colorless to slightly yellowish-colored and clear. 10 granule grains leave behind a neutral taste in the mouth after 30 s. A bittering power of under 0.1 is determined for the ground powder.

This corresponds to a reduction of the bittering power for pure verapamil HCl by 3 powers of 10.

Example 4

Production of Neutral-Taste Verapamil HCl Tablets 266.66 g of the ground hot melt compound described in example 5, 123.34 g of lactose D20, 180 g of Avicel PH 102, 30 g of Explotab® were mixed for 15 min in a double cone mixer at a speed of rotation of about 30/min and added through a sieve having a 1 mm mesh width. After this, 3 g of magnesium stearate are added and the mixture is mixed for a further 5 min.

The powder mixture is compressed to give tablets on a 1-die eccentric press (EKO type, Korsch, Berlin) at a pressure of about 155 MPa (35 tablets/min). The nominal weight is adjusted to 603 mg (corresponding to 80 mg of verapamil HCl).

Properties of the tablets:
Diameter 11.1 mm
Tensile strength: about 1.14 N/mm$^2$
Weight 595 mg (s: 5 mg)

The tablets obtained leave behind a neutral taste in the mouth after saliva wetting for 10 s. The release of active ingredient was about 36% after 30 min and about 55% after 60 min.

Example 5

Taste Isolation of a Cationic Active Ingredient Salt at a Molar Ratio of the Functional Groups in the Polymer to Verapamil of 1 mol to 0.42 mol A hot melt compound is produced from 40 parts by mass of verapamil HCl and 60 parts by mass of a copolymer of 40% by weight of methyl acrylate, 30% by weight of ethyl acrylate and 30% by weight of methacrylic acid. The temperature of the extruder cylinder was kept between 140° C. and 150° C. The speed of rotation of the screw was 150/min, the throughput was about 600 g/h. The mean residence time of the material in the extruder was about 4½ min. The granules produced from this extrusion process are colorless to slightly yellowish-colored and clear. 10 granule grains leave behind a neutral taste in the mouth after 30 s. A bittering power of under 10 is determined for the ground powder.

This corresponds to a reduction of the bittering power for pure verapamil HCl by a power of 10.

If 800 mg of the ground powder are stirred into 50 ml of completely demineralized water (corresponding to 8 mg of verapamil HCL per milliliter of water), a pH of 3.8 is determined.

Example 6

Production of Neutral-Taste Verapamil Tablets 200 g of the ground hot melt compound described in example 7, 190 g of lactose D20, 180 g of Avicel PH 102, 30 g of Explotab® were mixed for 15 min in a double cone mixer at a speed of rotation of about 30/min and added through a sieve having a 1 mm mesh width. After this, 3 g of magnesium stearate are added and the mixture is mixed for a further 5 min.

The powder mixture is compressed to give tablets on a 1-die eccentric press (EKO type, Korsch, Berlin) at a pressure of about 155 MPa (35 tablets/min). The nominal weight is adjusted to 603 mg (corresponding to 80 mg of verapamil HCl).

Properties of the tablets:
Diameter 11.1 mm
Tensile strength: about 1.26 N/mm$^2$
Weight 586 mg (s: 4 mg)

The tablets obtained leave behind a neutral taste in the mouth after saliva wetting for 10 s. The release of active ingredient was about 38% after 30 min and about 59% after 60 min.

Example 7

Taste Isolation of a Cationic Active Ingredient Salt at a Molar Ratio of the Functional Groups in the Polymer to Verapamil of 1 mol to 0.63 mol A hot melt compound is produced from 50 parts by mass of verapamil HCl and 50 parts by mass of a copolymer of 40% by weight of methyl acrylate, 30% by weight of ethyl acrylate and 30% by weight of methacrylic acid. The temperature of the extruder cylinder was kept between 140° C. and 150° C. The speed of rotation of the screw was 150/min, the throughput was about 600 g/h.

The mean residence time of the material in the extruder was about 4½ min. The granules produced from this extrusion process are colorless to slightly yellowish-colored and clear. 10 granule grains leave behind a neutral taste in the mouth after 30 s. A bittering power of under 10 is determined for the ground powder. This corresponds to a reduction of the bittering power for pure verapamil HCl by a power of 10.

If 800 mg of the ground powder are stirred into 50 ml of completely demineralized water (corresponding to 8 mg of verapmil per milliliter of water), a pH of 4 is determined.

Example 8

Production of Neutral-Taste Verapamil Tablets 160 g of the ground hot melt compound described in example 9, 230 g of lactose D20, 180 g of Avicel PH 102, 30 g of Explotab® were mixed for 15 min in a double cone mixer at a speed of rotation of about 30/min and added through a sieve having a 1 mm mesh width. After this, 3 g of magnesium stearate are added and the mixture is mixed for a further 5 min.

The powder mixture is compressed to give tablets on a 1-die eccentric press (EKO type, Korsch, Berlin) at a pressure of about 190 MPa (35 tablets/min). The nominal weight is adjusted to 603 mg (corresponding to 80 mg of verapamil HCl).

Properties of the tablets:
Diameter 11.1 mm
Press pressure: about 190 MPa
Tensile strength: about 2.83 N/mm$^2$
Weight 590 mg (s: 4 mg)

The tablets obtained leave behind a neutral taste in the mouth after saliva wetting for 10 s. The release of active ingredient was about 38% after 30 min and about 59% after 60 min.

Example 9

Taste Isolation of a Cationic Active Ingredient Salt at a Molar Ratio of the Functional Groups in the Polymer to Verapamil of 1 mol to 0.95 mol A hot melt compound is produced from 60 parts by mass of verapamil HCl and 40 parts by mass of a copolymer of 40% by weight of methyl acrylate, 30% by weight of ethyl acrylate and 30% by weight of methacrylic acid. The temperature of the extruder cylinder was kept between 140° C. and 150° C. The speed of rotation of the screw was 150/min, the throughput was about 600 g/h. The mean residence time of the material in the extruder was about 4½ min. The granules produced from this extrusion process are colorless to slightly yellowish-colored and clear. 10 granule grains leave behind a slightly bitter taste in the mouth after 30 s. A bittering power of under 10 is determined for the ground powder. This corresponds to a reduction of the bittering power for pure verapamil HCl by a power of 10.

If 800 mg of the ground powder are stirred into 50 ml of completely demineralized water (corresponding to 8 mg of verapamil per milliliter of water), a pH of 4 is determined.

Example 10

Production of Neutral-Taste Verapamil Tablets 133.32 g of the ground hot melt compound described in example 11, 256.68 g of lactose D20, 180 g of Avicel PH 102, 30 g of Explotab® were mixed for 15 min in a double cone mixer at a speed of rotation of about 30/min and added through a sieve having a 1 mm mesh width. After this., 3 g of magnesium stearate are added and the mixture is mixed for a further 5 min.

The powder mixture is compressed to give tablets on a 1-die eccentric press (EKO type, Korsch, Berlin) at a pressure of about 155 MPa (35 tablets/min). The nominal weight is adjusted to 603 mg (corresponding to 80 mg of verapamil HCl).

Properties of the tablets:
Diameter 11.1 mm
Tensile strength: about 1.65 N/mm$^2$
Weight 595 mg (s: 3 mg)

The tablets obtained leave behind a slightly bitter taste in the mouth after saliva wetting for 10 s. The release of active ingredient was about 56% after 30 min and about 77% after 60 min.

Example 11

Taste Isolation of a Cationic Active Ingredient Salt at a Molar Ratio of the Functional Groups in the Polymer to Verapamil of 1 mol to 1.47 mol A hot melt compound is produced from 70 parts by mass of verapamil HCl and 30 parts by mass of a copolymer of 40% by weight of methyl acrylate, 30% by weight of ethyl acrylate and 30% by weight of methacrylic acid. The temperature of the extruder cylinder was kept between 140° C. and 150° C. The speed of rotation of the screw was 140/min, the throughput was about 600 g/h. The mean residence time of the material in the extruder was about 4½ min. The granules produced from this extrusion process are colorless to slightly yellowish-colored and clear. 10 granule grains leave behind a slightly bitter taste in the mouth after 30 s. A bittering power of under 10 is determined for the ground powder. This corresponds to a reduction of the bittering power for pure verapamil HCl by a power of 10.

If 800 mg of the ground powder are stirred into 50 ml of completely demineralized water (corresponding to 80 mg of verapamil per milliliter of water), a pH of 4 is determined.

Example 12

Production of Neutral-Taste Verapamil Tablets 114.28 g of the ground hot melt compound described in example 13, 275.72 g of lactose D20, 180 g of Avicel PH 102, 30 g of Explotab® were mixed for 15 min in a double cone mixer at a speed of rotation of about 30/min and added through a sieve having a 1 mm mesh width. After this, 3 g of magnesium stearate are added and the mixture is mixed for a further 5 min.

The powder mixture is compressed to give tablets on a 1-die eccentric press (EKO type, Korsch, Berlin) at a pressure of about 155 MPa (35 tablets/min). The nominal weight is adjusted to 603 mg (corresponding to 80 mg of verapamil HCl).

Properties of the tablets:
Diameter 11.1 mm
Tensile strength: about 2.54 N/mm$^2$
Weight 602 mg (s: 3 mg)

The tablets obtained leave behind a markedly bitter taste in the mouth after saliva wetting for 10 s. The release of active ingredient was about 52% after 30 min and about 84% after 60 min.

Example 13

Production of a Neutral-Taste Verapamil HCl Syrup

In a stirring vessel, 1279.0 g of sucrose are heated to about 50° C. with 1139.9 g of water and stirred slowly until completely dissolved. After cooling to about 20° C., 37.6 g of the ground compound produced in example 9 are added and the mixture is homogenized for about 10 minutes. 27.3 g of a mixture of microcrystalline cellulose and Na carboxlmethylcellulose (Avicel RC 591®) and 2.8 g of Keltrol® F (polysaccharide B 1459) are now added to the suspension with stirring and the mixture is homogenized for about 15 min.

The syrup produced in this way is a homogeneous, white liquid with a sweet taste. The nominal active ingredient content is 8 mg/l.

The invention claimed is:

1. A process for the production of active ingredient-containing granules or powders comprising:
 a) melting of a mixture consisting essentially of a pharmaceutical active ingredient and a (meth)-acrylate copolymer which consists of 40 to 75% by weight of free radical-polymerized $C_1$- to $C_4$-alkyl esters of acrylic or of methacrylic acid and 25 to 60% by weight of (meth)acrylate monomers having an anionic group in the alkyl radical;
 b) extruding the mixture to obtain an extrudate; and
 c) comminuting the extrudate to give granules or powder; wherein
 a processing temperature of steps a) and b) is 10-50° C. above the glass transition temperature ($T_{mg}$) of the (meth)acrylate copolymer, wherein $T_{mg}$ is determined without plasticizer addition and in accordance with ISO 11357-2, item 3.3.3;
 the active ingredient is the salt of a basic substance; and
 the powder or granules obtained have a pH 7.0 or less.

2. The process as claimed in claim 1, wherein less than 0.1% by weight of release agents are added to the mixture.

3. The process as claimed in claim 1, wherein less than 0.5% by weight of plasticizers are added to the mixture.

4. The process as claimed in claim 1, wherein the quantitative ratio of active ingredient to (meth)acrylate copolymer is 10:1 to 1:10 based on parts by weight.

5. The process as claimed in claim 1, wherein the active ingredient, which is a salt of a basic substance, belongs to the active ingredient class of the analgesics, antirheumatics, psychopharmaceuticals, anti-biotics, beta-blockers, antidiabetics, H1 anti-histaminics, H2 antihistaminics, vitamins or mixtures thereof.

6. The process as claimed in claim 1, wherein the active ingredient salt is selected from the group consisting of verapamil HCl, levacetylmethadol hydro-chloride, oxycodone hydrochloride, oxycodone hydrochloride 3-water, tramadol hydrochloride, tilidine hydrochloride, prometazine embonate; prometazine hydrochloride, prometazine teoclate, donepezil hydrochloride, nefazodone hydrochloride, reboxetine mesilate, sertraline hydrochloride, erythromycin acistrate, erythromycin estolate, erythromycin ethylsuccinate, erythromycin gluco-heptonate, erythromycin lactobionate, erythromycin propionate, erythromycin stearate, erythromycin stinoprate, grepafloxacin hydrochloride, cipro-floxacin hydrochloride 1-water, levofloxacin hydrochloride, levofloxacin lactate, trovafloxacin mesylate, nevirapine hydrochloride, chlorhexidine acetate, chlorhexidine diacetate hydrate, chlorhexidine dihydrochloride, chlorhexidine digluconate, chlorhexidine gluconate, metro-nidazole benzoate, tetracycline hydrochloride, tetracycline phosphate, chlortetracycline hydro-chloride, oxytetracycline hydrochloride, doxy-cycline hyclate, minocycline hydrochloride hydrate, neomycin sulfate, tobramycin sulfate, clindamycin hydrochloride, moxifloxacin hydro-chloride, indinavir sulfate, saquinavir mesylate, nelfinavir mesylate, amatidine hydrochloride, streptomycin sulfate, amikacin bishydrogensulfate, paromomycin sulfate, tobramycin sulfate, propanolol hydrochloride, metoprolol tartrate, metoprolol fumarate, bisoprolol fumarate, nebivolol hydrochloride, betaxolol hydrochloride, tertatolol hydrochloride, bopindolol malonate, esmolol hydrochloride, oxprenolol hydrochloride, metformin hydrochloride, piogitazone hydro-chloride, rosiglitazone maleate, diphenhydramine acefyllinate, diphenhydramine citrate, diphen-hydramine hydrochloride, diphenhydramine mesilate, fexofenadine hydrochloride, cimetidine hydro-chloride, ticlopidine hydrochloride, ranitidine hydrochloride, roxatidine acetate, thiamine disulfide, thiamine disulfide O,—O-dinicotinate, thiamine hydrobromide, thiamine hydrochloride, thiamine nitrate, quinidine gluconate; hydrogen-sulfate 4-water; quinidine lactate, quinidine nitrite, quinidine polygalacturonate, quinidine sulfate, quinidine sulfate 2-water, amiloprilose, pseudoephedrine hydrochloride, sildenafil citrate, granisetrone hydrochloride, quinine sulfate 2-water; quinine monohydrochloride 2-water, meto-clopramide dihydrochloride 1-water; metoclopramide hydrochloride, pentoxyverine dihydrogencitrate, pentoxyverine hydrochloride and mixtures thereof.

7. The process as claimed in claim 6 wherein the pH of the granules or powder in aqueous suspension is pH 2.3 to pH 5.0.

8. The process as claimed in claim 1, wherein the $C_1$- to $C_4$-alkyl esters of acrylic or of methacrylic acid are selected from the group consisting of methyl methacrylate, ethyl methacrylate, butyl methacrylate, methyl acrylate, ethyl acrylate and butyl acrylate.

9. The process as claimed in claim 1, wherein the (meth)acrylate monomers having an anionic group in the alkyl radical are selected from the group consisting of acrylic acid and methacrylic acid.

10. The process as claimed in claim 1, wherein the (meth)acrylate monomer having an anionic group in the alkyl radical is methacrylic acid.

11. The process as claimed in claim 1, wherein the $C_1$- to $C_4$-alkyl esters of acrylic or of methacrylic acid are selected from the group consisting of methyl methacrylate, ethyl methacrylate, butyl methacrylate, methyl acrylate, ethyl acrylate and butyl acrylate; and the (meth)acrylate monomers having an anionic group in the alkyl radical are selected from the group consisting of acrylic acid and methacrylic acid.

12. The process as claimed in claim 11, wherein the (meth)acrylate monomer having an anionic group in the alkyl radical is methacrylic acid.

13. A process for the production of active ingredient-containing granules or powders according to claim 1, wherein the bittering power of the active ingredient-containing granules or powders produced is within the range between 1000 and 2000 as determined according to DAB (German pharmacopeia) 1999 method 2.8.N8 (determination of the bittering power).

14. A process for the production of active ingredient-containing granules or powders according to claim 1, wherein the bittering power of the active ingredient-containing granules or powders produced is 1000 or less than 1000 as determined according to DAB (German pharmacopeia) 1999 method 2.8.N8 (determination of the bittering power).

15. A process for the production of active ingredient-containing granules or powders according to claim 1, wherein more than 90% of the active ingredient in the dry product is in the form of a complex with the polymer.

16. A process for the production of active ingredient-containing granules or powders for oral administration according to claim 1, wherein more than 95% of the active ingredient in the dry product is in the form of a complex with the polymer.

17. A process for the production of active ingredient-containing granules or powders according to claim 1, wherein 28-56% of the active ingredient in the active ingredient-containing granules or powders produced by the process is released after 30 minutes from oral administration and 54-84% of the active ingredient in the active ingredient-containing granules or powders produced by the process is released after 60 minutes from administration.

18. An active ingredient-containing granules or powders, prepared by the process as claimed in claim 1.

19. A method of producing at least one pharmaceutical form or at least one precursor of pharmaceutical form comprising
preparing the active ingredient-containing granules or powder as claimed in claim 18 into at least one pharmaceutical form or at least one precursor of pharmaceutical form.

20. A process for the production of active ingredient-containing granules or powders for oral administration comprising:
a) melting of a mixture consisting essentially of a pharmaceutical active ingredient and a (meth)-acrylate copolymer which consists of 40 to 75% by weight of free radical-polymerized $C_1$- to $C_4$-alkyl esters of acrylic or of methacrylic acid and 25 to 60% by weight of (meth)acrylate monomers having an anionic group in the alkyl radical;
b) extruding the mixture to obtain an extrudate; and
c) comminuting the extrudate to give granules or powder;
wherein a processing temperature of steps a) and b) is 10-50° C. above the glass transition temperature ($T_{mg}$) of the (meth)acrylate copolymer, wherein $T_{mg}$ is determined without plasticizer addition and in accordance with ISO 11357-2, item 3.3.3; the active ingredient is the salt of a basic substance; and the granules or powders obtained have a pH 7.0 or less; and
wherein 28-56% of the active ingredient in the active ingredient-containing granules or powders produced by the process is released after 30 minutes from oral administration and 54-84% of the active ingredient in the active ingredient-containing granules or powders produced by the process is released after 60 minutes from oral administration.

21. A process for the production of active ingredient-containing granules or powders for oral administration according to claim 20, wherein the bittering power of the active ingredient-containing granules or powders produced is within the range between 1000 and 2000 as determined according to DAB (German pharmacopeia) 1999 method 2.8.N8 (determination of the bittering power).

22. A process for the production of active ingredient-containing granules or powders for oral administration according to claim 20, wherein the bittering power of the active ingredient-containing granules or powders produced is 1000 or less than 1000 as determined according to DAB (German pharmacopeia) 1999 method 2.8.N8 (determination of the bittering power).

23. A process for the production of active ingredient-containing granules or powders for oral administration according to claim 20, wherein more than 90% of the active ingredient in the dry product is in the form of a complex with the polymer.

24. A process for the production of active ingredient-containing granules or powders for oral administration according to claim 20, wherein more than 95% of the active ingredient in the dry product is in the form of a complex with the polymer.

25. A process for the production of active ingredient-containing granules or powders for oral administration according to claim 20, wherein the bittering power of the active ingredient-containing granules or powders produced is under 10 as determined according to DAB (German pharmacopeia) 1999 method 2.8.N8 (determination of the bittering power).

26. An active ingredient-containing granules or powders, prepared by the process as claimed in claim 20.

* * * * *